United States Patent
Barbeito et al.

(10) Patent No.: US 7,285,647 B2
(45) Date of Patent: Oct. 23, 2007

(54) FATTY ACID ESTERS OF ETHOXYLATED ALKYLGLUCOSIDES

(75) Inventors: Carmella A. Barbeito, Edison, NJ (US); Stuart Barry Polovsky, Matawan, NJ (US); Lowell Kreeger, Flemington, NJ (US)

(73) Assignee: The Lubrizol Corporation, Wickliffe, OH (US)

( * ) Notice: Subject to any disclaimer, the term of this patent is extended or adjusted under 35 U.S.C. 154(b) by 53 days.

(21) Appl. No.: 10/518,221

(22) PCT Filed: Jun. 13, 2003

(86) PCT No.: PCT/US03/18720

§ 371 (c)(1),
(2), (4) Date: Aug. 29, 2005

(87) PCT Pub. No.: WO04/000862

PCT Pub. Date: Dec. 31, 2003

(65) Prior Publication Data

US 2006/0099165 A1    May 11, 2006

Related U.S. Application Data

(60) Provisional application No. 60/390,074, filed on Jun. 19, 2002.

(51) Int. Cl.
*C07H 15/00* (2006.01)
(52) U.S. Cl. .................................................. 536/18.3
(58) Field of Classification Search ................ 536/18.3
See application file for complete search history.

(56) References Cited

U.S. PATENT DOCUMENTS

| | | | |
|---|---|---|---|
| 4,268,498 A | 5/1981 | Gedeon et al. | 424/59 |
| 4,364,930 A | 12/1982 | Griat et al. | 424/81 |
| 4,687,843 A | 8/1987 | Smolin et al. | 536/18.3 |
| 5,246,695 A | 9/1993 | Hintz et al. | 424/70 |
| 5,502,175 A * | 3/1996 | Desai et al. | 536/18.3 |
| 5,928,657 A | 7/1999 | Simon | 424/401 |

FOREIGN PATENT DOCUMENTS

| | | | |
|---|---|---|---|
| WO | 99/67017 | * | 12/1999 |
| WO | WO99/67017 | | 12/1999 |

OTHER PUBLICATIONS

Corresponding PCT International Publication No. WO 2004/000862 A1 published Dec. 31, 2003 and Search Report.

* cited by examiner

*Primary Examiner*—Deborah D. Carr
(74) *Attorney, Agent, or Firm*—Teresan W. Gilbert; Christopher D. Hilker

(57) ABSTRACT

A mixture of fatty acid esters of ethoxylated alkylglucosides of formula I is useful as a refatting agent in cosmetic formulations.

8 Claims, No Drawings

FATTY ACID ESTERS OF ETHOXYLATED ALKYLGLUCOSIDES

This application is a 371 of PCT/10503/18720 filed Jun. 13, 2003 which claims benefit of 60/390,074 filed Jun. 19, 2002.

The present invention relates to a mixture of fatty acid esters of ethoxylated alkylglucosides and their use in cosmetic compositions.

BACKGROUND OF THE INVENTION

Glucose derivatives, such as fatty acid esters of alkoxylated alkylglucosides, may be produced from renewable raw materials. Due to agricultural over-production the starting materials are low in cost and available in unlimited amounts. Therefore, much research efforts have been spent on the development of ethoxylated alkylglucosides and their uses.

U.S. Pat. No. 4,364,930 discloses a stable oil-in-water emulsion for use in cosmetic or pharmaceutical compositions. The emulsifying system comprises among other components a mixture of (1) mono- and/or dialkyl carboxylates of alpha-methyl glucoside and (2) mono- and/or dialkyl carboxylates of alpha-methyl glucoside which has been polyoxyethylenated with 10-30 moles of ethylene oxide.

U.S. Pat. No. 5,502,175 discloses fatty acid esters which are prepared by ethoxylating methylglucoside with from 84 to 300 moles, preferably 120 moles of ethylene oxide and subsequent esterification with 2-4 moles, preferably 1.8-3.5 moles of a saturated or unsaturated C1 fatty acid. The prepared fatty acids are used in shampoos and foam baths. They act as a thickening agent and have a good moisturizing effect and reduce irritation values of common ingredients, such as anionic and non-ionic surfactants.

U.S. Pat. No. 4,687,843 discloses esterified propoxylated methyl glucoside 25 compositions which are useful as skin moisturizers and emollients.

One object of the present invention is to find new acid esters of alkoxylated alkylglucosides. Another object of the present invention is to find acid esters of atkoxylated alkylglucosides which are useful in skin conditioning, and in particular as an enhancer of skin lipids, that means as a refatting agent.

SUMMARY OF THE INVENTION

One aspect of the present invention is a mixture of fatty acid esters of an ethoxylated alkylglucoside of formula I

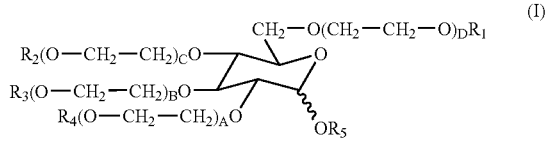

(I)

wherein the sum of A, B, C and D is from 10 to 60, each $R_1$, $R_2$, $R_3$ and $R_4$ independently is hydrogen or —C(O)-M, wherein M is a $C_{11}$-$C_{29}$ alkyl or alkenyl, and $R_5$ is a $C_1$-$C_5$ alkyl, provided that the ethoxylated alkylglucoside on the average comprises from 2.1 to 2.8—C(O)-M groups.

Another aspect of the present invention is a cosmetic composition which comprises the mixture of fatty acid esters.

Yet another aspect of the present invention is the use of the mixture of fatty acid esters as a refatting agent in a cosmetic composition.

Yet another aspect of the present invention is a process for preparing the mixture of fatty acid esters, which process comprises the steps of i) reacting an alkylglucoside with from 10 to 60 moles of ethylene oxide per mole of alkylglucoside and ii) reacting the ethoxylated alkylglucoside with from 2.1 to 2.8 moles of a saturated or unsaturated $C_{11}$-$C_{29}$ fatty acid or a C ester thereof.

DETAILED DESCRIPTION OF THE INVENTION

The fatty acid esters of the ethoxylated alkylglucosides of the present invention are a mixture of molecules with different degrees of esterification such that the compounds of formula I on the average comprise from 2.1 to 2.8, preferably from 2.2 to 2.7, more preferably from 2.3 to 2.5, most preferably about 2.4—C(O)-M groups.

Generally the degree of ethoxylation of the individual molecules also varies somewhat, as it is typical for oligomers. However, the average degree of ethoxylation, that means the sum of A, B, C and D is from 10 to 60, preferably from 25 to 50, more preferably from 30 to 40, most preferably about 35. A, B, C and D each independently can have the meaning of from 0 to 60, provided that the sum of A, B, C and D is from 10 to 60.

In formula I M is $C_{11}$-$C_{29}$ alkyl or alkenyl, preferably $C_{11}$-$C_{19}$ alkyl or alkenyl, more preferably $C_{16}$-$C_{18}$ alkenyl, most preferably a $C_{17}$ alkenyl group. The alkyl and alkenyl group may be branched, but preferably it is straight.

In formula I $R_5$ is an alkyl group of from 1 to 5 carbon atoms, preferably from 1 to 3 carbon atoms, most preferably methyl.

The fatty acid esters of the present invention can be prepared by preparing first a mixture of fatty acid esters of an alkylglucoside and then ethoxylating the product. However, according to a preferred process the fatty acid esters are prepared by ethoxylating an alkylglucoside and subsequent esterification.

The ethoxylation can be accomplished in one, two or more steps. The reaction temperature generally is from 100 to 190° C., preferably from 130 to 160° C., more preferably from 145 to 155° C. The reaction pressure generally is from 100 to 1000 kPa, preferably from 200 to 600 kPa, more preferably from 250 to 550 kPa.

When carrying out the ethoxylation step in one step, an alkylglucoside, preferably methylglucoside, is ethoxylated with from 10 to 60, preferably from 25 to 50, more preferably from 30 to 40, most preferably with about 35 moles of ethylene oxide per mole of the alkylglucoside. Generally a basic catalyst is used, preferably an alkali metal hydroxide, more preferably potassium or sodium hydroxide. The amount of catalyst generally is from 0.2 to 5 weight-percent, preferably from 0.5 to 2.5 weight-percent, based on dry alkylglucoside. The ethoxylation is generally conducted under an inert atmosphere using a gas like argon, helium, or preferably nitrogen. The ethoxylation is generally completed within 2 to 6 hours.

In an alternate embodiment of the present invention the ethoxylation is accomplished in two steps. An ethoxylated alkylglucoside which preferably comprises from 5 to 25 moles, more preferably from 10 to 20 moles, most preferably about 20 moles of groups derived from ethylene oxide per mole of alkylglucoside, is used as starting material for further ethoxylation. The preferred starting materials are commercially available from Amerchol Corp. under the trademark Glucam E-10 or Glucam E-20. The ethoxylated alkylglucoside is converted to the corresponding alkoxide salt by reacting the ethoxylated alkylglucoside with a base, preferably an alkali metal hydroxide, most preferably with potassium or sodium hydroxide. The alkali metal hydroxide is preferably used as a 0.1 to 1 weight percent, more preferably 0.25 to 0.5 weight percent, aqueous solution. The ethoxylation is carried out as described above with a corresponding smaller amount of ethylene oxide.

The subsequent esterification is effected by direct esterification with from 2.1 to 2.8, preferably from 2.2 to 2.7, more preferably from 2.3 to 2.5, most preferably about 2.4 moles of a fatty acid or by transesterification with a corresponding amount of a fatty acid ester.

The fatty acid used for direct esterification is a saturated or unsaturated $C_{11}$-$C_{29}$ fatty acid, preferably a $C_{11}$-$C_{19}$ fatty acid, more preferably a $C_{16}$-$C_{18}$ fatty acid or a blend of such fatty acids. Preferred fatty acids are stearic acid, linoleic acid, linolenic acid, lauric acid, palmitic acid, undecanoic acid, or most preferably oleic acid. The direct esterification with a saturated or unsaturated $C_{11}$-$C_{29}$ fatty acid can be carried out according to a process known in the art, for example by an acid catalyzed reaction.

For transesterification $C_{1\text{-}4}$-alkyl esters of the mentioned $C_{11}$-$C_{29}$ fatty acids are preferred, more preferably the methyl esters of the mentioned $C_{11}$-$C_{29}$ fatty acids. Methyl oleate is the most preferred fatty acid ester. The transesterification is generally conducted in the presence of a base catalyst. The catalyst is preferably an alkali metal hydroxide, such as potassium or sodium hydroxide. Generally from 0.03 to 1 weight percent, preferably from 0.1 to 0.5 weight percent of base catalyst is used, based on the weight of ethoxylated alkylglucoside. The reaction temperature generally is from 130 to 200° C., preferably from 160 to 185° C., more preferably from 170 to 180° C. The reaction is preferably conducted under vacuum. More preferably, the vacuum starts at about 125 mm Hg and ends at about 3 mm Hg. The reaction typically takes about 4 to 6 hours.

The above-described mixture of fatty acid esters is useful in cosmetic compositions, particularly in skin cleansing compositions. Cleansing the skin does not only remove dirt but also removes fats and oils, which leaves the skin feeling dry and taut. Therefore, the cosmetic industry spends much research efforts to find conditioning agents which are useful in skin cleansing compositions. This presents a major challenge, since a refatting agent should fulfill a variety of requirements. It should enhance skin lipids by leaving the skin smoother, less dry, and a causing a positive tactile sensation. It should not unduly increase the viscosity of the cleansing composition, otherwise the cleansing composition is not pourable and not accepted by the consumers. Also, the refatting agent should not provide an unpleasant odor or color to the cleansing composition. It should not adversely affect clarity or foaming and be compatible with other cleansing ingredients.

It has surprisingly been found that the above-described mixture of fatty acid esters of ethoxylated alkylglucosides is useful as a refatting agent in cosmetic formulations, such as skin cleansing compositions. The mixture of fatty acid esters is generally a clear or slightly hazy liquid with a viscosity low enough to be pourable. It has generally a light yellow color.

The cosmetic composition of the present invention generally comprises from 0.1 to 10, preferably from 0.5 to 5, more preferably from 1 to 3 weight percent of the mixture of fatty acid esters, based on the total weight of the cosmetic composition. Cosmetic compositions comprising the preferred fatty acid esters of the present invention have shown favorable results in sensory assessments wherein after-feel in skin washing tests are evaluated. It has also been found that the mixture of fatty acid esters does not adversely affect the foaming of cleansing formulation, but produces a creamier foam.

The cosmetic composition of the present invention may comprise a number of additives known in the art, such as water, surfactants, thickeners, conditioning agents, humectants, preservatives, perfumes, and colorants.

The present invention is further illustrated by the following examples which should not be construed to limit the scope of the present invention. All parts and percentages are by weight unless otherwise indicated.

EXAMPLE 1

A 1.5 liter glass pressure reactor, equipped to automatically feed ethylene oxide based on pressure, is charged with 589 g of ethoxylated methylglucoside (comprising 20 moles of ethylene oxide units per mole of methylglucoside) which contains about 0.25 weight percent potassium hydroxide. The contents of the reactor are heated and the reactor is evacuated when the temperature of the contents reaches about 130° C. Heating is continued. When the temperature of the reactor contents reaches about 145° C., the reactor is pressurized with nitrogen to about 450 kPa (about 50 psig). The pressure is released to about 180 kPa (about 10 psig). This nitrogen pressurizing and releasing is repeated twice more. The reactor is then pressurized to about 275 kPa (about 23 psig). When the temperature of the contents reaches 155° C., ethylene oxide is fed into the reactor. The ethylene oxide feed rate is controlled so that the reactor pressure never exceeds about 550 kPa (about 65 psig). After about 376 g of ethylene oxide have been feed to the reactor, the ethylene oxide feed is stopped and the reactor is held at 155° C. for 30 minutes to essentially react any remaining ethylene oxide. The reaction is cooled and the contents discharged to yield about 965 g of recovered ethoxylated alkylglucoside comprising about 35 units derived from ethylene oxide per unit of alkylglucoside. The product is designated as E-35.

For esterification of the ethoxylated alkylglucoside a laboratory round bottom glass reactor is charged with 100 grams of E-35 as prepared above, 41 g of methyl oleate, and 0.1 g of hypophosphorous acid. A nitrogen sparge is initiated and the contents of the reactor are heated to 175° C. while applying vacuum. The vacuum is about 125 torrs. The reaction is held at 175° C. with this vacuum for 30-60 minutes. The vacuum is then slowly increased to maximum, about 3 torrs and the reaction held under these conditions for about 4 to 5 hours. The reaction mixture is cooled. Once its temperature is below 80° C., it is neutralized with about 0.4 g of 88% aqueous lactic acid. The reactor contents are discharged and about 138 g of product are recovered. Based on weights charged, the product can be described as a mixture of fatty acid esters of ethoxylated methylglucoside comprising on average 35 moles of groups derived from ethylene oxide and on average 2.4 moles of ester groups per mole of methylglucoside.

The product is a slightly viscous, clear liquid and light yellow in color.

quality and quantity of foam and feel of the foam. The panelist then places a glove on the other hand and repeats the procedure with the other formulation, noting again the quality and quantity of the foam and feel of the foam.

The panelist rinses both hands, pats dry, and once fully dried, determines the feel of each hand with the other to determine any difference in after-feel. The percentage of people expressing a preference for the formulation of Example 1, 2 or 3 respectively over the formulation of Comparative Example A, the percentage of people expressing a preference for the formulation of Comparative Example A and the percentage of people expressing no preference are listed in Table 1 below.

| | Evalulation foam quantity and quality | | | After-feel sensory evaluation | | |
|---|---|---|---|---|---|---|
| Example | Preference for invention | Preference for Comp. Ex. A | No preference | Preference for Comp. Ex. A | Preference for invention | No preference |
| 1 | 55 | 40 | 5 | 33 | 27 | 40 |
| 2 | 40 | 55 | 5 | 15 | 35 | 50 |
| 3 | 55 | 40 | 5 | 35 | 20 | 45 |

EXAMPLE 2

Example 1 is repeated except that that only about 37.6 grams of methyl oleate is used. The produced mixture of fatty acid esters of ethoxylated methyl glucoside comprises on average 35 moles of groups derived from ethylene oxide and on average 2.2 moles of ester groups per mole of methylglucoside.

EXAMPLE 3

Example 1 is repeated except that 47.8 grams of methyl oleate is used. The produced mixture of fatty acid esters of ethoxylated methylglucoside comprises on average 35 moles of groups derived from ethylene oxide and on average 2.8 moles of ester groups per mole of methylglucoside.

Refatting Tests

The products of Examples 1-3 above are compared in a sensory test with PEG-7 Glycerol Cocoate (polyoxyethylene (7) glyceryl monococoate), which is commercially available as Cetiol HE (Trademark) from Cognis, and which is a leading refatting agent in the US market.

A formulation consisting of 9% sodium laureth-2 sulfate, commercially available as Standapol ES-2 (Trademark) from Cognis; 4% cocamidopropyl betaine, commercially available as Velvetex BK-35 (Trademark) from Cognis, 1% decyl glucoside, commercially available as Plantaren 2000 (Trademark) from Cognis, and 85% water is prepared.

To produce the formulation of Examples 1-3, 1% of the product of Example 1, 2 or 3 is added to the formulation. To produce the formulation of Comparative Example A, 1% of Cetiol HE (Trademark) is added to the formulation.

A panel study of 20 people is conducted. Initially the panelist washes both hands with Ivory (Brand name) soap bar, and then places a latex glove on one hand and washes the other hand with approximately one gram of either the formulation of one of the Examples 1-3 or with the formulation of Comparative Example A. The panelist notes the

What is claimed is:

1. A mixture of fatty acid esters of an ethoxylated alkylglucoside of formula I

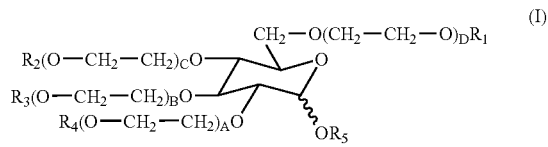

wherein the sum of A, B, C and D is from 30 to 40, each $R_1$, $R_2$, $R_3$, and $R_4$, independently is hydrogen or —C(O)—M, wherein M is a $C_{11}$-$C_{29}$ alkyl or alkenyl, and $R_5$ is a $C_1$-$C_5$ alkyl, provided that the ethoxylated alkylglucoside on the average comprises from 2.1 to 2.8-C(O)—M groups.

2. The mixture of claim 1 wherein the ethoxylated alkylglucoside on the average comprises from 2.3 to 2.5-C(O)—M groups.

3. The mixture of claim 1 wherein M in formula I is a $C_{17}$ alkenyl group.

4. The mixture of claim 1 wherein $R_5$ is methyl.

5. A cosmetic composition comprising the mixture of fatty acid esters of claim 1.

6. The cosmetic composition of claim 5 being a skin cleansing composition.

7. A method of using the mixture of fatty acid esters of claim 1 as a refatting agent in a cosmetic composition.

8. A process for preparing the mixture of claim 1 comprising the steps of:
   i) reacting an alkylglucoside with from 30 to 40 moles of ethylene oxide per mole of alkylglucoside and
   ii) reacting the ethoxylated alkylglucoside with from 2.1 to 2.8 moles of a saturated or unsaturated $C_{11}$-$C_{29}$ fatty acid or a $C_{1-4}$-alkyl ester thereof.

* * * * *